(12) United States Patent
Karapetyan (10) Patent No.: US 9,693,844 B1
(45) Date of Patent: Jul. 4, 2017

(54) DENTAL TOOL CLEANING DEVICE

(71) Applicant: Armen Karapetyan, Los Angeles, CA (US)

(72) Inventor: Armen Karapetyan, Los Angeles, CA (US)

( * ) Notice: Subject to any disclaimer, the term of this patent is extended or adjusted under 35 U.S.C. 154(b) by 323 days.

(21) Appl. No.: 14/545,207

(22) Filed: Apr. 7, 2015

(51) Int. Cl.
*B08B 9/00* (2006.01)
*A61C 19/00* (2006.01)

(52) U.S. Cl.
CPC ............. *A61C 19/002* (2013.01); *B08B 9/00* (2013.01)

(58) Field of Classification Search
CPC .................... A61C 17/0202; A61C 17/036
USPC ............................ 134/22.19, 151, 114, 143
See application file for complete search history.

(56) References Cited

U.S. PATENT DOCUMENTS

| | | | | |
|---|---|---|---|---|
| 4,552,163 A * | 11/1985 | Biancalana | ............... | B08B 3/08 134/102.3 |
| 4,892,112 A * | 1/1990 | Knetsch | ............... | A61C 19/002 118/302 |
| 5,165,503 A * | 11/1992 | Hoffman | ................. | A61C 1/052 184/105.3 |
| 5,415,248 A * | 5/1995 | Eibl | ...................... | A61C 19/002 184/55.1 |
| 5,505,218 A * | 4/1996 | Steinhauser | ............ | A61L 2/025 134/102.1 |
| 5,961,937 A * | 10/1999 | Gobbato | ............... | A61C 19/002 134/104.2 |
| 7,771,544 B2 * | 8/2010 | Helfenbein | .......... | A61C 19/002 134/169 C |
| 8,439,677 B2 * | 5/2013 | Numakawa | .......... | A61C 19/002 134/166 C |
| 2004/0154652 A1 * | 8/2004 | Karapetyan | ............. | B08B 3/102 134/151 |
| 2013/0037047 A1 * | 2/2013 | Saiger | ..................... | A61L 2/025 134/1 |
| 2013/0312793 A1 * | 11/2013 | Ionidis | ................... | A61B 19/34 134/22.19 |

* cited by examiner

*Primary Examiner* — Nina Bhat (57) ABSTRACT

The present dental tool cleaning device generally provides a possibility to clean the burrs and brushes (files) of the remained tooth material on them after operation on patient. An improved dental tool cleaning device includes a container, comprising a lower portion which includes a neck with an opening and a first lid with a first nozzle, and an upper portion which includes a second lid comprising a second nozzle and an inlet fluid connector with the fluid channel.

8 Claims, 7 Drawing Sheets

DENTAL TOOL CLEANING DEVICE

FIELD OF THE INVENTION

A cleaning device for dental and/or medical tool provides a possibility to clean the burrs and brushes, files of the remained tooth material on them after operation on patient.

This invention is generally related to an apparatus intended for medical and/or dental tool cleaning and more particularly for cleaning treatment of the dental burrs and files (brushes) used in the drilling and handpiece tool.

BACKGROUND OF THE INVENTION

The dental tools, such as the burrs and brushes (files) of high speed and/or low speed dental drill or handpieces, are in wide use, and a dentist will commonly use the same dental tool especially the burrs and brushes for performing several dental operations on different patients in a short period of time. Furthermore, a routine is needed that would help to insure that all portions of a burrs and files, which have been exposed to one patient's mouth, are cleaned of the remained tooth material on the tool prior to sanitize and use with other patients. Such additional procedure would provide one more safeguard against the spread of disease. There is a need for a convenient, economical and effective apparatus/devices to help the dentist and his or her staff to clean (and later to sanitize) the tools between operations on patients.

The various types of the equipment/devices for cleaning of the dental removable tool are well known.

Similar equipment already exists, e.g. that described in U.S. Pat. No. 4,552,163. The medical/dental instrument/tool to be cleaned is placed vertically into a cylindrical chamber and jets of water and/or disinfectant mixed with air, are directed towards the vertical axis of the chamber and strike specific points of the front of the instrument. After striking the instrument, the jets rebound towards the walls of the chamber where gravity causes them to fall downwards. Consequently, there are a number of areas which are not sprayed or only partially sprayed by said liquids, thereby leaving an unwanted bacterial residue. This is particularly true in the lower part of the chamber where (for example, for the case of dental tool cleaning) there are usually areas which are more contaminated by the plaque debris. This is an unresolved and worrying problem.

Another analogous instrument/device for cleaning of a dental, medical or similar tools is described in the U.S. Pat. No. 5,961,937. The device comprises a chamber, preferably frusto-conical in shape or downward tapering, two walls separated by a hollow space, subdivided along axis into smaller spaces. The walls are connected to the interior of the chamber by rings of holes with downward pointing jets, and passing at a predetermined distance from the axis of the chamber. These jets clean/sterilize the entire internal and external surface area of the instrument along it length. The pressure upstream of the holes, their diameter and direction, ensures that the lower and more contaminated part of the instrument is more thoroughly treated.

Specifically, this prior art at the base of the chamber has a normal mesh type filter, which can be easily removed and washed or replaced, and a standard type chamber, operating on the Venturi principle, comprising a pipe, fitted with a nozzle, which blasts a jet of air to remove the contaminated water following the use of an instrument. Pipes lead from the manifold, to the valves control the various stages of the cleaning cycle.

The dirty tool is placed in the chamber without disconnecting it from the electric or pneumatic cable and the water cooling pipe, the reasons for which are twofold. When dental tool is inserted into the chamber, a cellulose pierceable membrane is out in place, impregnated with cleaning (e.g. water) or disinfecting (e.g., chemicals) fluid. This membrane is fixed in position at the opening by means of a ring nut and is pierced when the dirty dental tool is placed inside.

The pierced membrane, is removed on completion of the cleaning cycle before removing the instrument, or else is wound on by means of a miniature motor and is then re-wound into a special container, for dispensing cellulose membrane, which is removed when full.

The pneumatic cylinder or pump aspirates a single dose of cleaning or disinfecting fluid from the cartridge through the chamber, and then sends it on to the loading chamber, controlled by the sensor. The sensor senses the presence of the fluid and allows the cycle to proceed. At the pre-arranged moment, the valve opens, and the single dose is sent to the nebulizer whence it passes into the manifold which sends it on to the cylinder with the help of the valves. During the initial washing and drying stage of the instruments, the valves 3 open and a mixture of air and water is sent through the manifold and washes the dental tool. The air is sent through valve to the discharge point to create an aspiration effect in the chamber. One of the valves then closes and other valves remain open, sending the air to the manifold to dry the instrument and, simultaneously, to the discharge point, to continue the aspiration effect.

The device is of conical or tapered shape (wide at the mouth and narrow at the base). The device also includes four rings and holes, with the passing off center at a predetermined distance, from the axis of the chamber and inclined downwards at a defined angle. Thus, a swirling effect is produced around the dental tool/instrument (e.g. a single dental burr), in a downward direction towards the head of the dental burr, causing solid and non-solid particles on the head to be detached and drawn towards the discharge point. The dimensions of the holes are such that the fluid flowing from them strikes the instrument to be treated with a kinetic force which increases as it flows downwards from the top to the lower part of the chamber where the burr's head, i.e. the most contaminated part, is located. In addition, during the disinfecting cycle, particular attention has been given to the problem of pathogens inside a dental instrument caused, as already mentioned, by the aspirating action of the instrument inside the patient's mouth whilst deactivated, to prevent a loss of the cooling water.

The cleaning apparatus by U.S. Pat. No. 5,415,248 provides the cleaning and/or lubrication of the medical/dental tool. This apparatus for cleaning dental tools includes an instrument connection for blowing oil and/or cleaning agent, possibly in the form of a spray mist, through the instruments and subsequently drying the instruments with compressed air. The control of the various cleaning phases and of the conveyance of the cleaning liquids takes place pneumatically. In particular, a short-term flow of compressed air displaces at least one piston against a spring which causes oil and/or cleaning agent to be pressed into the instrument. A control edge of the piston produces a connection between the compressed air supply and the instrument connection when the piston leaves its upper position of rest. When the piston travels back in the opposite direction under the force of the spring after the short-term flow of compressed air has ended, the supply of oil and/or cleaning agent to the instrument connection is interrupted, while the supply of compressed air is maintained until the piston has again reached its upper position of rest. In the mentioned apparatus an external compressed air is supplied to the apparatus and reaches a tee in which a pressure reduction and/or a purification by means of an inserted filter may be carried out. The compressed air reaches from the tee through a line to an actuating button which starts the cleaning procedure when being pressed down. When the button is pressed downwardly against the force of a spring, the supply of compressed air and the continuing line are connected to each other for a relatively short time, so that compressed air is conducted from the tee through the actuating button to the head of a regulating unit. A piston is provided in the interior of the regulating unit. A spring presses the piston upwardly against the head of the regulating unit. When compressed air is admitted to the regulating unit, the piston is pressed downwardly against the force of the spring, and the piston rod, constructed as a double piston, presses oil into the line and cleaning agent into the line. A return flow of the two fluids into the lines is prevented by check valves in the cleaning agent line and by two analogous check valves in the oil line.

Such apparatus is complex and expensive.

Another apparatus by U.S. Pat. No. 4,892,112 also provides the cleaning and/or lubricating of the medical/dental tool, i.e. the care of dental instruments which is connectable at its inlet to a pressurized gas source and at its outlet to the inlet sleeve of the dental instrument to be serviced, which hand tool is provided with at least one container for receiving the agent and connected to the pressurized gas line leading form the inlet to the outlet of the hand tool. The apparatus permits a troublefree metering in of even highly viscous agents for the care of the instrument and the dispensing of various amounts of the agents. This is achieved by providing a pressure control valve from which a pressurized gas line leads to the outlet of the hand tool downstream of the inlet of the hand tool and by providing at least one pump for conveying the agent, the intake line of the pump being connected with the at least one container for receiving the agent and the pressure line being connected with the pressurized gas line leading to the outlet of the hand tool in a site downstream of the pressure control valve and upstream of the outlet of the hand tool. The apparatus includes a pressurized gas source, preferably the dental unit provided in each dental practice, is connected at the inlet of the hand tool. The tool is plugged onto the turbine tube in place of the turbine angle piece by means of the provided quick-turn coupling, if no such coupling is provided, it is screwed onto the thread of the tube. On actuating the foot pedal of the dental unit, namely on turning on the turbine angle piece not present now, air is introduced into the hand tool with the flow pressure adjusted for the turbine of normally about bar. A pressure control (safety) valve reduces this pressure to about bar without subjecting the tubes of the dental unit to stress. The compressed air is now further conveyed through the pressurized gas line to the outlet where turbine angle pieces and tool holders and angle pieces of the most diverse kinds (not represented), termed dental instruments for short in the following, can be plugged on by means of exchangeable and sealing adapters, for instance the elastic connecting sleeves. The apparatus also comprises two storage containers for cleaning (disinfecting) and lubricating agents from which these cleaning and lubricating agents, called agents for short in the following, are sucked via intake lines by means of two manually actuated reciprocating pumps and can be injected under pressure independently of one another into the pressurized gas line, so that the pressurized gas charges the agents into the dental instrument plugged on. For this purpose, the pressure line emanates from each pump and terminates together with the pressurized gas line in a metering or mixing chamber disposed in flowing direction upstream of the outlet, etc.

This apparatus requires the pump presence and has the same deficiency as the above described apparatus, i.e. such apparatus is complex and expensive.

Another U.S. Pat. No. 5,505,218 provides the cleaning of the dental tool in a washing container filled with liquid, particularly water, using the ultrasonic effect. The device comprises a pot-shaped washing container with a multiplicity of mountings in the interior of the container each for one tool holder/handpiece (tooth drill), a water supply system, with which water can be supplied to the washing container and can also be lead from it, a compressed air supply system, a care agent supply system and an ultrasonic cleaning device, of which only one ultrasonic transducer for applying ultrasound to the washing container is illustrated. The washing container has a supply and discharge line, which is part of the water supply system, and with a water outlet. The following are arranged downstream of each other in the direction of flow, in the water supply line which is connected to a water connection: a first solenoid valve, a pump, a softening device and a condenser. The softening device is connected directly to the water outlet by means of a discharge line in which two solenoid valves are arranged one behind the other, so that the waste water can be directly discharged into the water outlet. Also, device includes the compressed air supply system having five compressed air lines connected in parallel, an electrically powered air heater, etc.

Such apparatus does not provide the cleaning of the dental burrs and brushes and is used for the handpiece and mostly drills cleaning.

The cleaning apparatus for medical and/or dental tool, described in the U.S. Pat. No. 6,948,505. This apparatus provides a possibility to clean the burrs and brushes (files) of the remained tooth material on them after operation on patient. An improved cleaning apparatus for medical and/or dental tool includes a container, comprising a neck with an opening and at least one of a plurality of apertures located in the lower part of the neck, a fluid stream reflector of a lid, which includes a connector comprising inlet pipe, which is coupled by a tubular means with a fluid line via controllable valve. The cleaning apparatus for medical and/or dental tool includes a spherical form container, which includes support rested on the rims of the hollow cylindrical stand connected to the base. Also, the container includes an upper portion (neck) significantly smaller in diameter from the lower portion of the container. The apparatus also includes a gasket and a fluid stream reflector in the form of a ring of the truncate conical configuration. The fluid stream reflector is rigidly connected to the lid. The fluid stream reflector is intended for reflection of the exhausted agent (liquid/water) in the direction down. The neck includes the apertures located in the lower part of the neck. The longitudinal (horizontal) axes of the apertures is coincident with the upper half-portion of the fluid stream reflector. The apparatus has the predetermined ratio of diameter of the container to diameter of the apertures and the predetermined ratio of diameter of the container to inside diameter of the fluid outlet portion to provide the efficient turbulence of the cleaning fluid inside container. The dental tools (e.g., burrs, files, etc.) are placed inside container. The lid, including fluid stream reflector, is assembled with the gasket and connector and coupled with the neck of the container. The container is installed in the cylindrical stand and rested by its support on the rim of the cylindrical stand connected to the base in order to provide the stable position of the container during cleaning process. The excess of the agent is exhausted (outstreamed, drained) from the container through the apertures. The outstream of the excess fluid is reflected by the fluid stream reflector in the direction down. The fluid stream reflector provides the prevention of sprinkle of the excess fluid all over around in the horizontal direction through the apertures.

This cleaning apparatus is complex and expensive

Thus, there is a great need in the art for the improved dental (medical) tool cleaning device, providing non-complex, not expensive, convenient, economical and effective cleaning of the dental tool (e.g. burrs and files/brushes) exposed to one patient's mouth of the remained tooth material, plaque debris on the tool between operations on patients, thereby providing a safeguard against the spread of disease by discharging the contaminated substances and residuals.

OBJECT AND ADVANTAGES OF THE INVENTION

Accordingly, several objects and advantages of the present invention are to provide convenient, economical and effective cleaning of the dental/medical tool.

It is another object of the invention to eliminate necessity of the hand-labor process of the dental/medical tool cleaning.

It is still another object of the invention to reduce the time of the dental/medical tool cleaning.

It is further object of the invention to increase a safeguard against the spread of disease.

It is still further object of the invention to provide a non-complex device for dental tool cleaning.

It is still further object of the invention to provide a not expensive device for dental tool cleaning.

It is still further object of the invention to provide a convenient device for dental tool cleaning.

It is still further object of the invention to provide an economical device for dental tool cleaning.

It is still further object of the invention to have a device aproviding effective cleaning of the dental tool.

Still, further objects and advantages will become apparent from a consideration of the ensuing description accompanying drawings.

BRIEF DESCRIPTION OF THE DRAWINGS

In order that the invention and the manner in which it is to be performed may be more clearly understood, embodiments thereof will be described by way of example with reference to the attached drawings, of which.

SUMMARY OF THE INVENTION

A cleaning device for dental (and/or medical) tool provides a possibility to clean the burrs and brushes (files) of the remained tooth material on them after operation on patient. An improved dental tool cleaning device includes a container, comprising a lower portion which includes a neck with an opening and a first lid with a first nozzle, and an upper portion which includes a second lid comprising a second nozzle and an inlet fluid connector with the fluid channel.

DETAILED DESCRIPTION OF THE INVENTION

Here the description of an improved dental tool cleaning device will be done in statics (as if the components of the improved apparatus are suspended in the space) with description of their relative connections to each other. The description of the functional operations of an improved device will be done hereinafter.

An improved cleaning device (FIG. 1) includes a container 1, comprising a lower portion 2 which includes a neck 3 (FIGS. 2, 3, 7, 9, 10) with an opening 4 and a first lid 5 with a first nozzle 6, and an upper portion 7 which includes a second lid 8 comprising a second nozzle 9 and an inlet fluid connector 10.

The lower portion 2 also includes an outer thread 11 of the neck 2 for coupling with an inner tread 12 of the first lid 5. The first nozzle 6 of the first lid 5 also comprises an opening 13, diameter "$d_2$" is less than the diameter "$d_1$" of the opening 4 of the lower portion 2 of the container 1 of the improved dental tool cleaning device.

Figure 6:
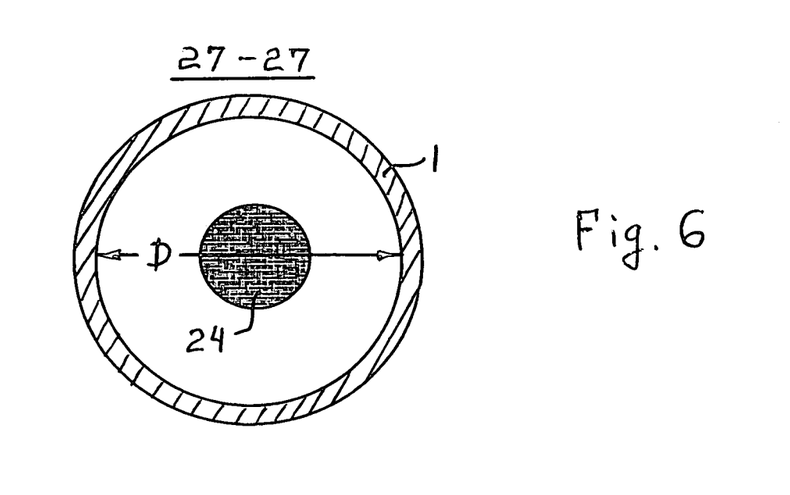
FIG. 6 is a simplified cross-sectional drawing 27-27 of an improved dental tool cleaning device.

The inner diameter "$d_2$" of opening 13 of the first nozzle 6 is a function of (depend on) the correlation of the inner diameter "D" of the container 1 (FIGS. 2, 6) and inner diameter "$d_1$" of opening 4 of the lower portion 2 of the container 1, i.e.:

$$d_2 = f_1(D, d_1) \qquad [1]$$

wherein:
  $d_2$—an inner diameter of the opening 13 of the first nozzle 6;
  $f_1$—a symbol of function;
  D—an inner diameter of the container 1;
  $d_1$—an inner diameter of the opening 4 of the lower portion 2 of the container 1.

Only for example, if the inner diameter "D" will be approximately 4.0 sm (D=4.0 sm=40 mm), the inner diameter "$d_1$" of opening 4 of the lower portion 2 of the container 1 will be approximately 2.0 sm ($d_2$=2.0 sm=20 mm), the inner diameter "$d_2$" of the opening 13 of the first nozzle 6 will be approximately 1.0 sm ($d_2$=1.0 sm=10 mm).

The second lid 8 of the upper portion 7 of the container 1 also includes an inner thread 14 for coupling with an outer thread of 15 of the upper portion 7 of the container 1. The second nozzle 9 comprises a fluid channel 16 extended from a fluid channel 17 (FIGS. 2, 3, 5, 8) of the inlet fluid connector 10. The inlet portion 18 of the inlet fluid connector 10 includes a groove 19 for the tight connection with the fluid flow tubular portion/means (not shown).

Figure 2:
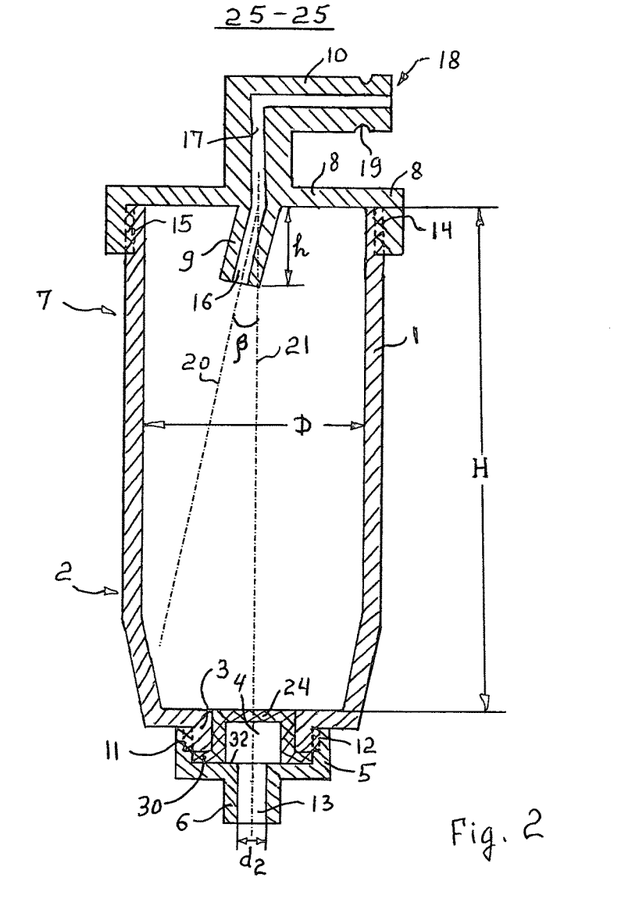
FIG. 2 is a full cross-sectional drawing 25-25 of an improved dental tool cleaning device.

The second nozzle 9 is directed to the lower portion 2 of the container 1, as shown in FIG. 2. The axis 20 of the fluid channel 16 of the second nozzle 9 is located under angle "β" which is a function of (depend on) the correlation of the inner diameter "D" of container 1, length "H" of the container 1 (excluding length of the neck 3), and length "h" of second nozzle 9, i.e.:

$$\beta = f_2(D,H,h) \quad [2]$$

wherein:
β—an angle between axis 20 of the fluid channel 16 of the second nozzle 9 and axis 21 of the container 1;
$f_2$—a symbol of function;
D—an inner diameter of the container 1;
H—a length of container 1 (excluding length of the neck 3);
h—a length of nozzle 9.

Only for example, if the inner diameter "D" will be approximately 4.0 sm (D=4.0 sm=40 mm), the length "H" will be approximately 11.0 sm (H=11.0 mm=110 mm) and the length "h" of the nozzle 9 will be approximately 2.0 sm (h=2.0 sm=20 mm), the angle "β" will be approximately 30° 03=30°).

Figure 3:
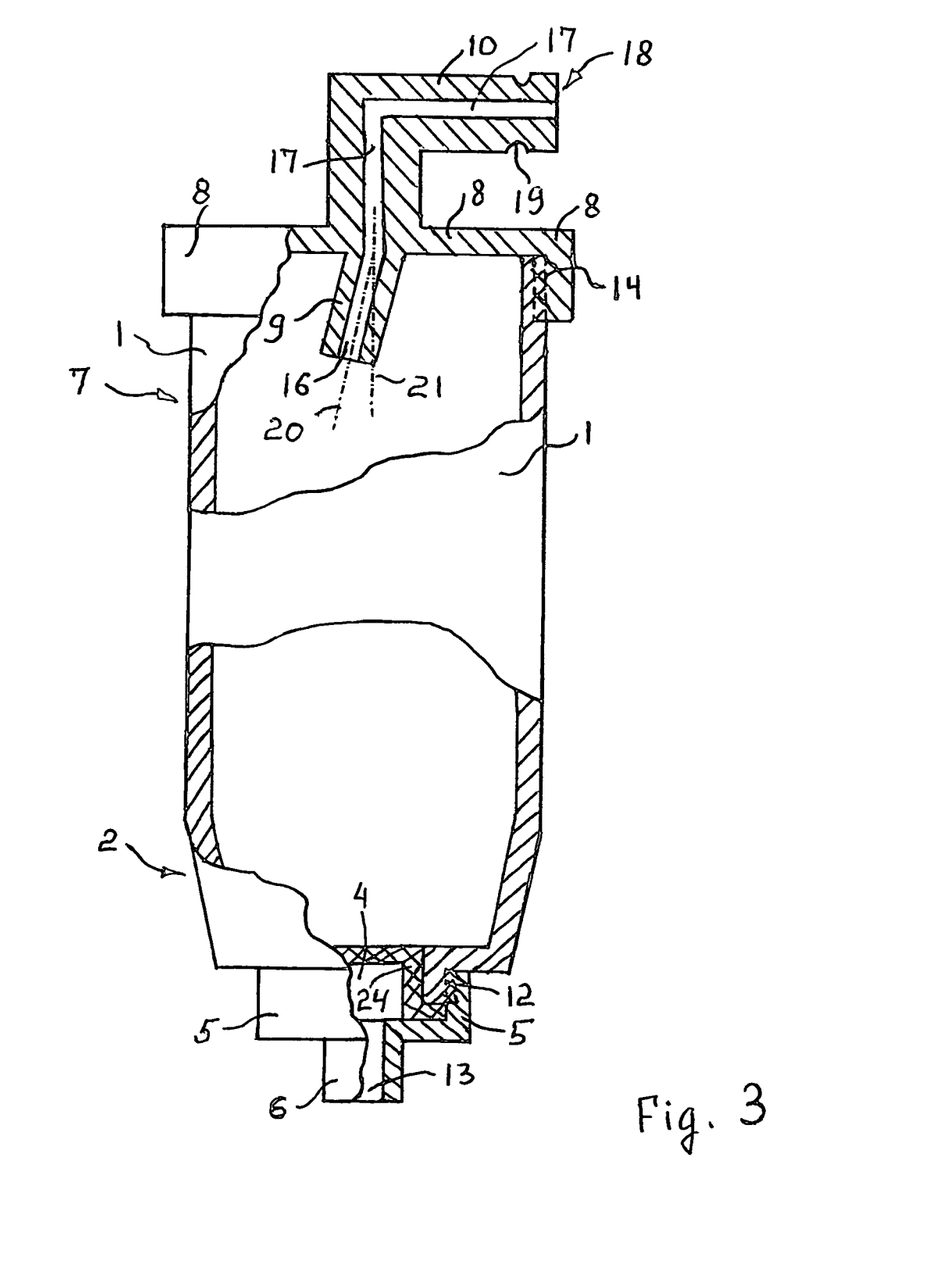
FIG. 3 is a simplified first illustration of an improved dental tool cleaning device.
Figure 4:
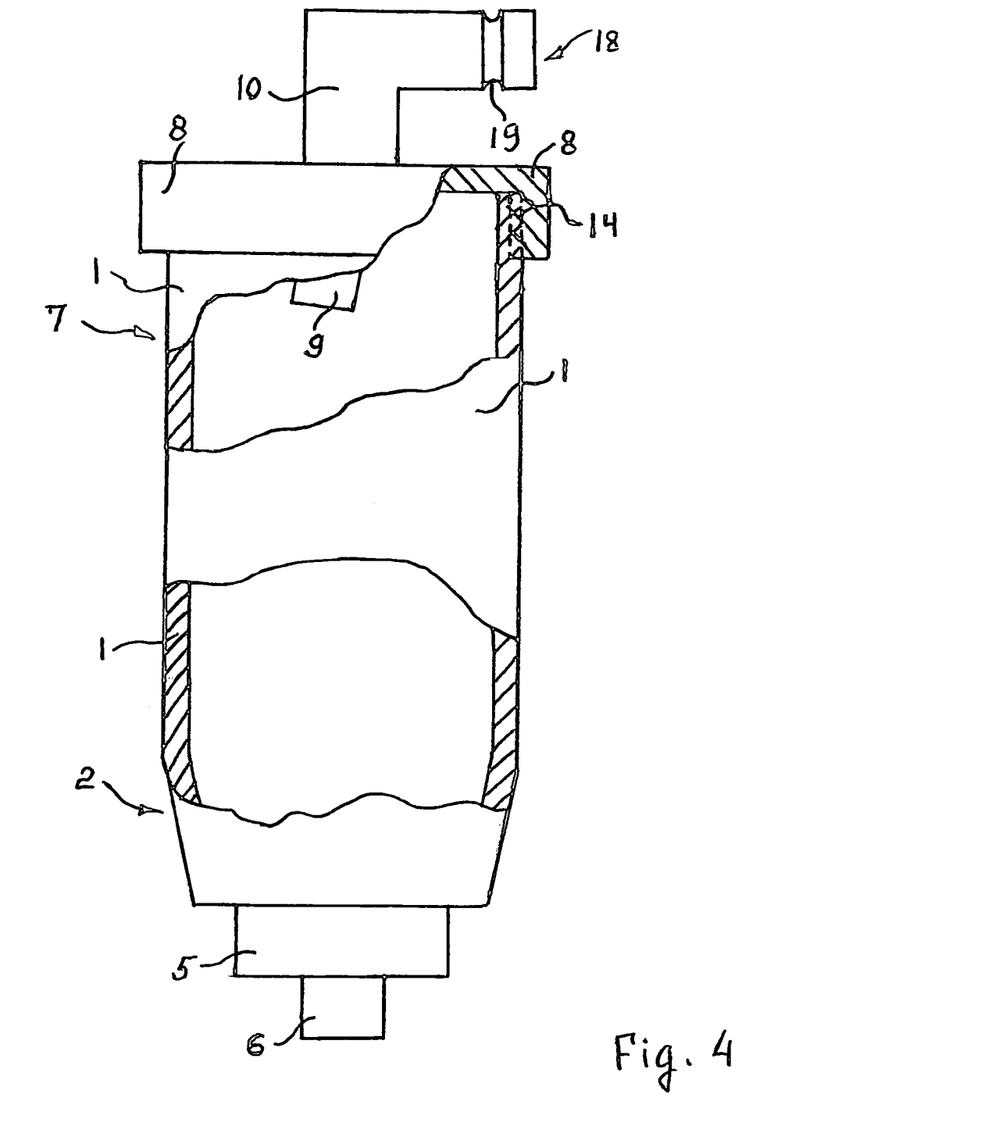
FIG. 4 is a simplified second illustration of an improved dental tool cleaning device.
Figure 5:
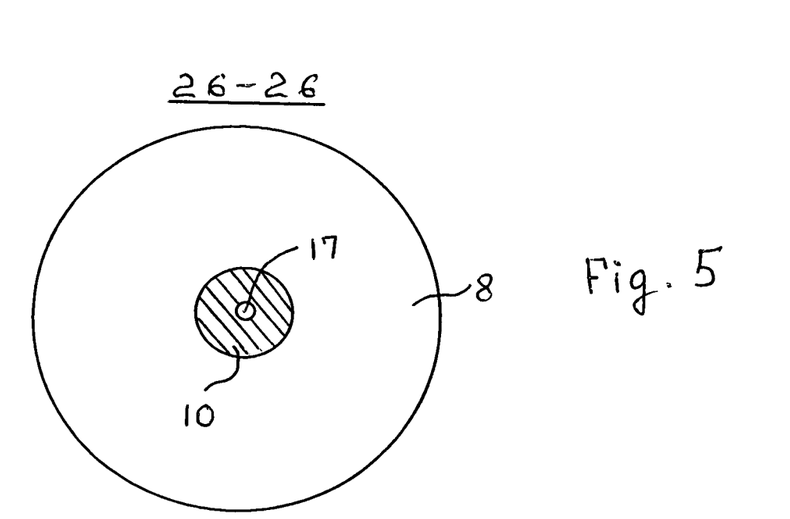
FIG. 5 is a simplified cross-sectional drawing 26-26 of an improved dental tool cleaning device.
Figure 7:
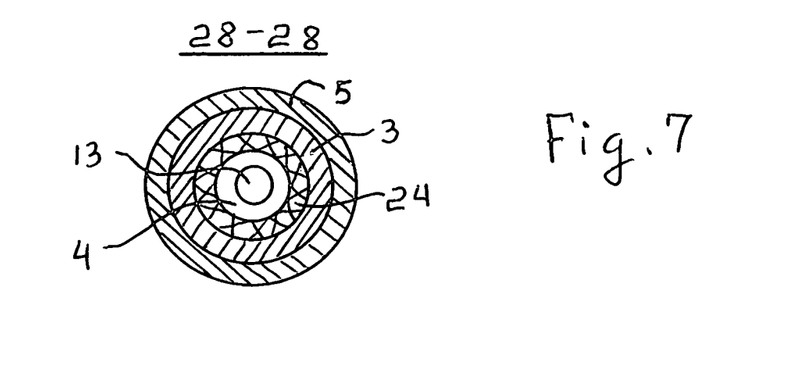
FIG. 7 is a simplified cross-sectional drawing 28-28 of an improved dental tool cleaning device.
Figure 8:
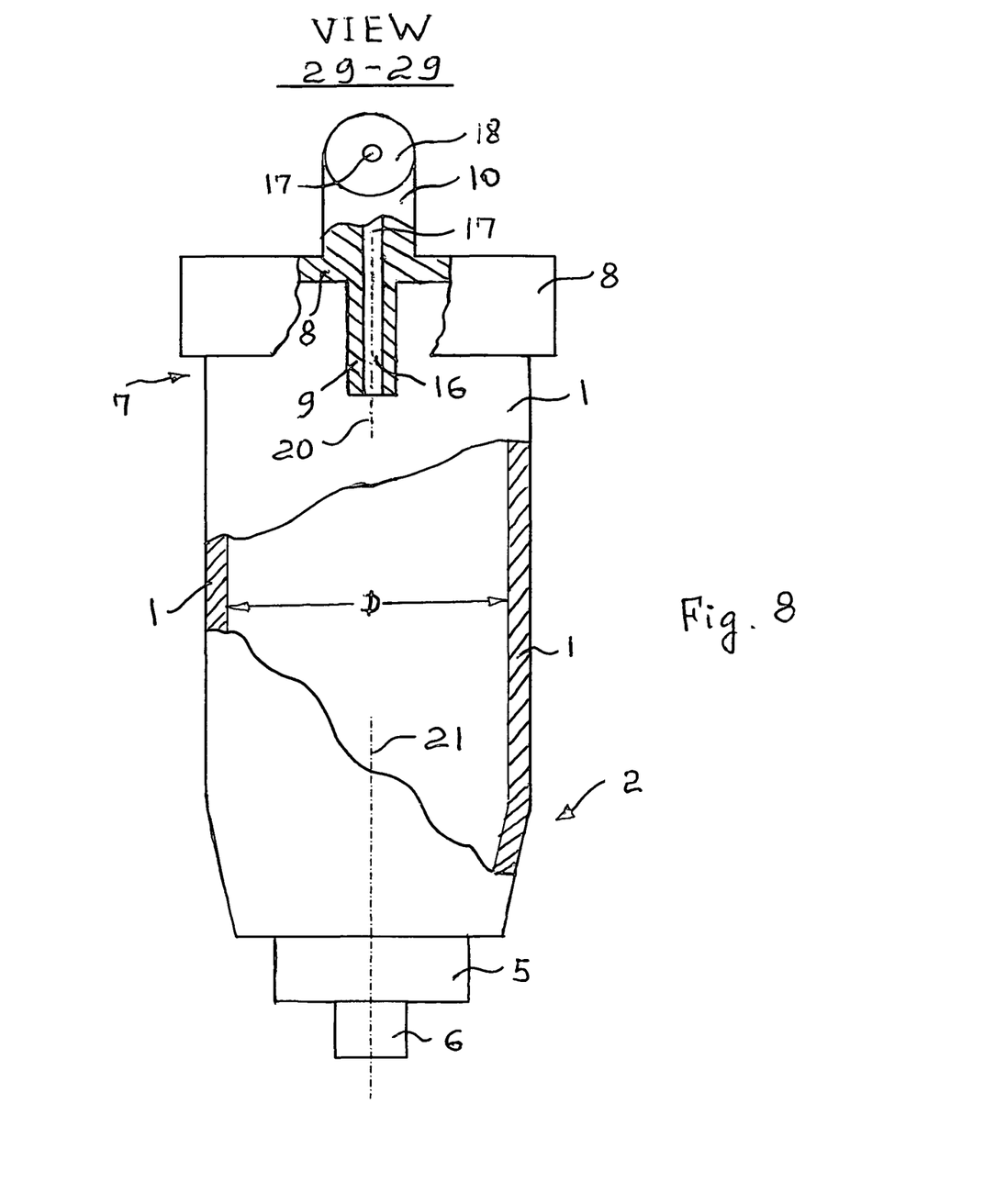
FIG. 8 is a simplified partial cross-sectional view 29-29 of an improved dental tool cleaning device.
Figure 10:
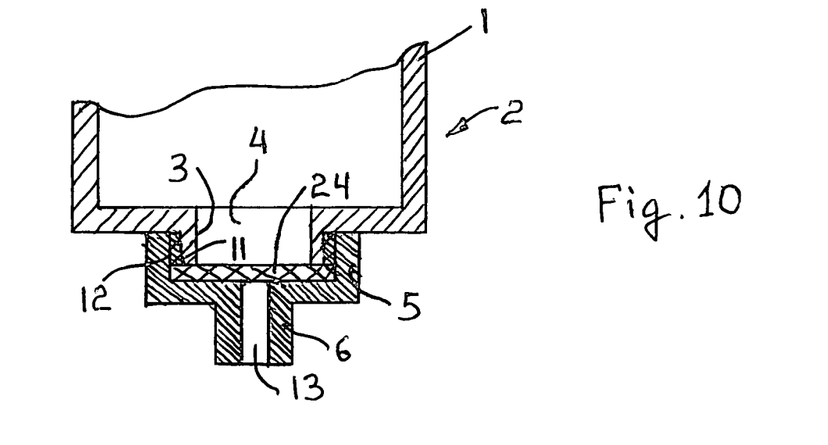
FIG. 10 is a simplified cross-sectional drawing of the neck assembly with the flat screen and with the second variant of a lower portion of a container of an improved dental tool cleaning device.

The improved dental tool cleaning device also includes a screen 24 (FIGS. 2, 3, 7), preventing the exhausting of the dental tool (not shown) through the opening 4 in the neck 3 of the lower portion 2 and through the opening 13 of the first nozzle 6. Preferably, the neck 3 should not be long. Under this condition, the screen 24 can be of a flat configuration, as shown in FIG. 10, instead of to be of the cylindrical configuration, as shown in FIGS. 2, 3, 7. The short neck 3 with the flat screen 24 will prevent the dental tool from to be stacked into the neck area without circular movements into container 1.

The lower portion 2 of the container 1 can have a cylindrical configuration (FIG. 10), or truncate conical configuration (a conical portion 22 in FIG. 1, 2, 3, 4, 8), or curved configuration (a convex portion 23 in FIG. 9) or any other reasonable configuration and form, as well as the configurations (forms) of the nozzles 6, 9 and lids 5, 8.

Figure 1:
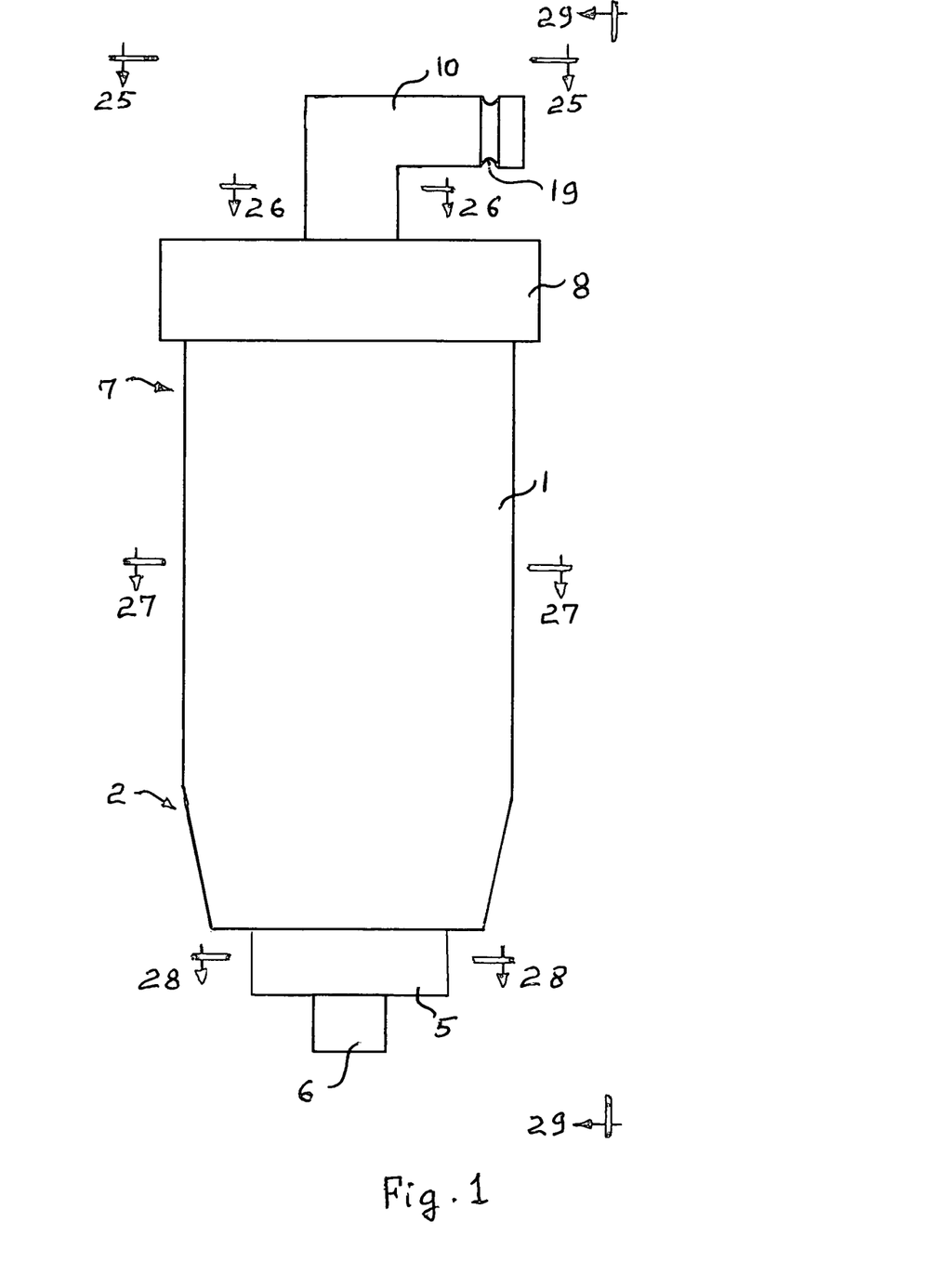
FIG. 1 is a simplified drawing of an improved dental tool cleaning device.
Figure 9:
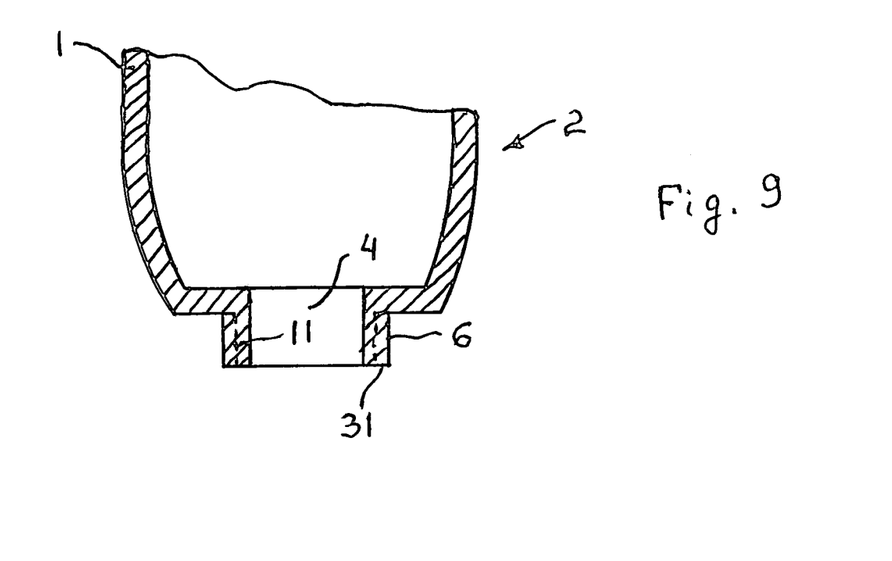
FIG. 9 is a simplified cross-sectional drawing of the first variant of a lower portion of a container of an improved dental tool cleaning device.

The upper portion 7 of the container 1 can have a cylindrical configuration, as shown in FIG. 1, 2, 3, 4, 8) or conical configuration (not shown), or curved configuration (not shown), analogously to the lower portion 2, shown in FIG. 2 and FIG. 9 respectively, or any other reasonable configuration and form. The inlet fluid connector 10 can be of straight configuration (not shown) instead of to be bent under angle of 90°, as shown in FIGS. 1, 2, 3, 4.

According to FIG. 2, the second nozzle 9 is located in the center of the second lid 8, but the second nozzle(s) 9 can be located in any reasonable place(s) of the second lid 8, and can have an axis 20 be directed to any reasonable area of the container 1.

The FIGS. 2-4, 8 depict the single second nozzle 9, but the second lid 8 can include more than one (single) second nozzle (not shown), thereby providing higher turbulent effect inside container 1.

Additionally, the first 6 and second 9 nozzles, the inlet fluid connector 10 are extended from the lids, as shown in FIGS. 2 and 3, but they can have a separate configuration, and can be rigidly attached (e.g., glued, etc.) to the lids. Also, the coupling of the first lid 5 to the container 1 and coupling of the second lid 8 to the neck 3 can be provided by any other reasonable principles of coupling (not shown), for example by lock coupling (not shown) or by clipping devices (not shown), etc., instead of by threads.

All components of the improved dental tool cleaning device can be made from any reasonable material, appropriate for the medical/dental implementation, but preferably from the transparent plastic material, especially for the container 1. It is also should be understandable that the components of the improved dental tool cleaning device can be of any reasonable forms and dimensions too. The components of the improved dental tool cleaning device, shown in FIGS. 1-10, have the "sharp" (e.g., 90°) corners, but the corners can have the rounded configuration. The equations [1] and [2] are herein given as an additional descriptive explanation for the person(s) skilled in the art for enablement of the improved dental tool cleaning device.

The improved dental tool cleaning device operates as follows below. The reasonable quantity of the dental tool (not shown) is inserted in the container 1 of the improved dental tool cleaning device. The reasonable quantity of the dental tool, needed to be cleaned, presumes that the inserted dental tool will be able to move inside the container 1 under the fluid stream (not shown) power. The first 5 and second 8 lids are coupled with the container 1.

The screen 24 of a cylindrical configuration (form) is installed in the neck 3, as shown in the FIGS. 2, 3, 7, wherein the flange 30 of the cylindrical screen 24 is installed between the rim 31 of the neck 3 and the inner surface 32 of the first lid 5. Referring to FIG. 10, the screen 24 of a flat configuration is installed between the rim 31 of the neck 3 and the inner surface 32 of the first lid 5.

Any appropriate chemicals can be used as a fluid. The water, as a fluid instead of chemicals, can be used for cleaning of the dental tool too. The sink's valve (not shown) or any other water distributing means (not shown) is connected to one end of the fluid flow tubular portion/means (not shown), and another end of the fluid flow tubular portion/means (not shown) is connected to the inlet portion 18 of the inlet fluid connector 10.

The fluid (for example, a water) from the sink's valve (facet) [not shown] or from any other water distributing means (not shown) through the fluid flow tubular portion/means (not shown) connected to the sink's valve (not shown) and to the inlet portion 18 flows through the fluid channel 17 of the inlet fluid connector 10 to the fluid channel 16 of the second nozzle 9.

The fluid stream (not shown) from the second nozzle 9 is directed along axis 20 (FIG. 2) of the fluid channel 16 to the lower portion 2 of the container 1, thereby providing circular movements of the dental tool (not shown) inside the container 1 of the improved cleaning device, thereby cleaning the dental burrs, files, brushes, etc. from the plaque debris and of the remained tooth material on them after dental operation on patient. The extra fluid is exhausted from the container 1 through the screen 24, opening 4 in the neck 3 of the lower portion 2, and through the opening 13 of the first nozzle 6 of the first lid 5.

CONCLUSION, RAMIFICATION AND SCOPE

Accordingly the reader will see that, according to the invention, I have provided a dental tool cleaning device, providing convenient, economical and effective cleaning of the dental tool (e.g. burrs, files, brushes, etc.) exposed to one patient's mouth of the remained tooth material and/or plague debris on the tool between operations on patients. An improved cleaning device for medical and/or dental tool has various possibilities, considering activities of the cleaning devices.

While the above description contains many specificities, these should be not construed as limitations on the scope of the invention, but as exemplification of the presently-preferred embodiments thereof. Many other ramifications are possible within the teaching to the invention. For example, an improved cleaning apparatus for medical and/or dental tool eliminates the necessity of the dentist's staff hand-labor activity, providing more time for them to use on patients. Also an improved cleaning device can be used for disinfecting agent too, thereby providing a higher degree of safeguard.

Thus, the scope of the invention should be determined by the appended claims and their legal equivalents, and not by examples given.

There has thus been outlined, rather broadly, the more important features of the invention. In this respect, it is understood that the invention is not limited in its application to the details of arrangements of the components/portions/elements set forth in the description and/or drawings. The invention is capable of other embodiments and of being practiced and carried out in various ways.

Also, it is to be understood that the phraseology and terminology employed herein are for the purpose of description and should not be regarded as limiting.

The persons of ordinary skills and/or creativity in the art will readily observe that numerous modifications and advantages of the improved device may be made while retaining the teachings of the invention.

As such, those skilled in the art will appreciate that the conception, upon which this disclosure is based, can readily be utilized as a basis for the designing of other structures, for carrying out the several purpose of the present invention. It is important, therefore, that the claims be regarded as including such equivalent constructions insofar as they do not depart from the spirit and scope of the present invention.

THE DRAWING REFERENCE NUMERALS

1.—a container;
2.—a lower portion of container 1;
3.—a neck;
4.—an opening of the lower portion 2;
5.—a first lid;
6.—a first nozzle;
7.—an upper portion of container 1;
8—a second lid;
9—a second nozzle;
10.—an inlet fluid connector;
11.—an outer thread of the neck 3;
12.—an inner thread of the first lid 5;
13.—an opening of the first nozzle 6;
14.—an inner thread of the second lid 9;
15.—an outer thread of the upper portion 7;
16.—a fluid channel of the second nozzle 9;
17.—a fluid channel of fluid connector 10;
18.—an inlet portion of the fluid connector 10;
19.—a groove;
20.—an axis of fluid channel 16;
21.—an axis of container 1;
22.—a conic portion of lower portion 2;
23.—a convex portion of lower portion 2;
24.—a screen;
25-25—a full cross-section of an improved dental tool cleaning device;
26-26—a cross-section of an improved dental tool cleaning device;
27-27—a cross-section of an improved dental tool cleaning device;
28-28—a cross-section of an improved dental tool cleaning device;
29-29—a cross-sectional view of an improved dental tool cleaning device;
30.—a flange of screen 24 of a cylindrical configuration;
31.—a rim of the neck 3;
32.—an inner surface of the first lid 5.

What is claimed is:

1. A dental tool cleaning device comprising a cylindrical container including an upper cylindrical portion and lower cylindrical portion wherein said lower portion of said container includes neck and a first lid, said lid further including, a first nozzle and wherein said lid includes an inner thread coupling with the outer thread of said neck; said first nozzle including openings for exhausting of a fluid; said upper portion of said container further comprising a fluid connector inlet comprising a fluid channel and an inlet portion; wherein said inlet portion includes a groove; and disposed within said lower portion of said container further including a second lid comprising at least one second nozzle, wherein said second lid includes a fluid channel extended from said fluid channel of said inlet fluid connector; an outer thread of said upper portion of said container for coupling with an inner thread of said second lid; a screen of a cylindrical form, wherein said screen of cylindrical form is installed in said opening in said neck of said lower portion of said container of said dental tool cleaning device, and further comprising a flange installed between a rim of said neck and an inner surface of said first lid.

2. The dental tool cleaning device of claim 1, wherein said second nozzle is centrally located in said second lid.

3. The dental tool cleaning device of claim 1, wherein said second lid include a plurality of second nozzles.

4. The dental tool cleaning device of claim 1, wherein the lower portion of said cylindrical container is a truncate conic form.

5. The dental tool cleaning device of claim 1, wherein the lower portion of said cylindrical container is a convex form.

6. The dental tool cleaning device of claim 1, wherein said screen is installed in a flat from between said rim of said neck and said inner surface of said first lid thereby securing said screen in position of said container.

7. The dental tool cleaning device of claim 1, wherein the first lid and said neck is coupled together with a locking device.

8. The dental tool cleaning device of claim 1, wherein said second lid is coupled to said upper portion of said container with a locking device.

* * * * *